(12) United States Patent
Nishijima et al.

(10) Patent No.: US 11,497,108 B2
(45) Date of Patent: *Nov. 8, 2022

(54) RADIATION IMAGING SYSTEM

(71) Applicant: Konica Minolta, Inc., Tokyo (JP)

(72) Inventors: Yuuichi Nishijima, Mitaka (JP); Tetsu Hosoki, Koganei (JP); Nobuyuki Miyake, Yokohama (JP)

(73) Assignee: KONICA MINOLTA, INC., Tokyo (JP)

( * ) Notice: Subject to any disclaimer, the term of this patent is extended or adjusted under 35 U.S.C. 154(b) by 140 days.

This patent is subject to a terminal disclaimer.

(21) Appl. No.: 17/002,214

(22) Filed: Aug. 25, 2020

(65) Prior Publication Data

US 2021/0076477 A1 Mar. 11, 2021

Related U.S. Application Data

(63) Continuation of application No. 15/228,416, filed on Aug. 4, 2016, now Pat. No. 10,806,015.

(51) Int. Cl.
*H05G 1/08* (2006.01)
*A61B 6/00* (2006.01)
*G08B 21/18* (2006.01)

(52) U.S. Cl.
CPC ............. *H05G 1/08* (2013.01); *A61B 6/4494* (2013.01); *A61B 6/46* (2013.01); *A61B 6/465* (2013.01); *A61B 6/467* (2013.01); *A61B 6/485* (2013.01); *A61B 6/486* (2013.01); *A61B 6/487* (2013.01); *A61B 6/488* (2013.01); *G08B 21/18* (2013.01)

(58) Field of Classification Search
CPC ......... A61B 6/461; A61B 6/566; A61B 6/545; A61B 6/03; A61B 6/469; H04N 5/225; H05G 1/60; H05G 1/30; G06T 2207/10081
See application file for complete search history.

(56) References Cited

U.S. PATENT DOCUMENTS

2006/0188064 A1 8/2006 Razzano et al.
2011/0050403 A1 3/2011 Liu et al.
2011/0208048 A1 8/2011 Arima
(Continued)

FOREIGN PATENT DOCUMENTS

CN 1541615 A 11/2004
CN 102551755 A 7/2012
(Continued)

OTHER PUBLICATIONS

CNIPA Notification of Reexamination for corresponding CN Application No. 201610638560.9; dated Oct. 21, 2021.
(Continued)

*Primary Examiner* — Don K Wong
(74) *Attorney, Agent, or Firm* — Cantor Colburn LLP

(57) ABSTRACT

A radiation imaging system includes a radiation source and a notifying unit. The radiation source is for still image shooting and moving image shooting performed by the radiation imaging system to obtain image data of a subject. The notifying unit notifies whether a type of imaging to be performed is the still image shooting or the moving image shooting in a mode in which the type is instinctively recognizable by at least one of sense of sight, sense of hearing, and sense of touch.

13 Claims, 13 Drawing Sheets

(56) References Cited

U.S. PATENT DOCUMENTS

| | | |
|---|---|---|
| 2012/0002012 A1 | 1/2012 | O'Grady et al. |
| 2012/0130238 A1* | 5/2012 | Muraoka .............. A61B 6/4233 |
| | | 600/436 |
| 2013/0168558 A1 | 7/2013 | Tsuchiya |
| 2014/0098933 A1 | 4/2014 | Profio et al. |
| 2015/0042677 A1 | 2/2015 | Shimamura et al. |

FOREIGN PATENT DOCUMENTS

| | | |
|---|---|---|
| JP | 2002117415 A | 4/2002 |
| JP | 2002263088 A | 9/2002 |
| JP | 2012110451 A | 6/2012 |
| JP | 2014516503 A | 7/2014 |
| JP | 2015100530 A | 6/2015 |

OTHER PUBLICATIONS

Extended European Search Report corresponding to Application No. 16182529.4; dated Jan. 11, 2017.

JPO Notice of Reasons for Refusal corresponding to Application No. 2015-156645; dated Dec. 4, 2018.

CNIPA First Office Action corresponding to Application No. 201610638560.9; dated Nov. 28, 2018.

CNIPA Office Action for corresponding CN Application No. 201610638560.9 dated Apr. 1, 2019.

SIPO Third Office Action corresponding to Application No. 201610638560.9; dated Aug. 2, 2019.

CNIPA Decision of Rejection corresponding to Application No. 201610638560.9; dated Nov. 1, 2019.

JPO Notice of Reasons for Refusal for corresponding JP Application No. 2019-109987; dated Jul. 7, 2020.

USPTO Non Final Office Action for U.S. Appl. No. 15/228,416 dated Dec. 18, 2018.

CNIPA Office Action/Search Report for corresponding CN Application No. 201610638560.9; dated Apr. 28, 2021.

JPO Decision of Refusal for corresponding JP Application No. 2019-109987; dated Nov. 5, 2020.

CNIPA Office Action with Search Report for corresponding CN Application No. 201610638560.9; dated Feb. 10, 2022.

* cited by examiner

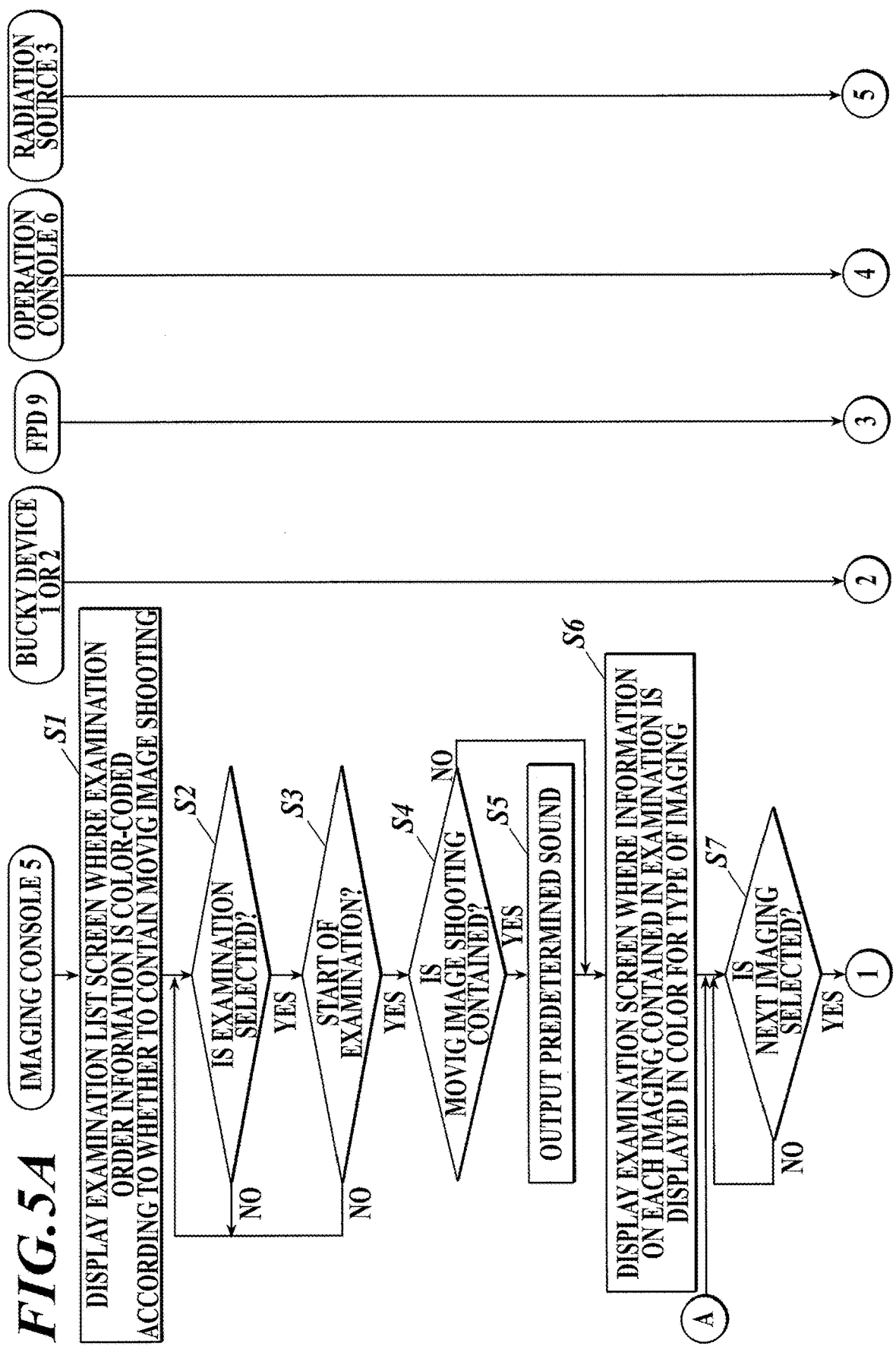

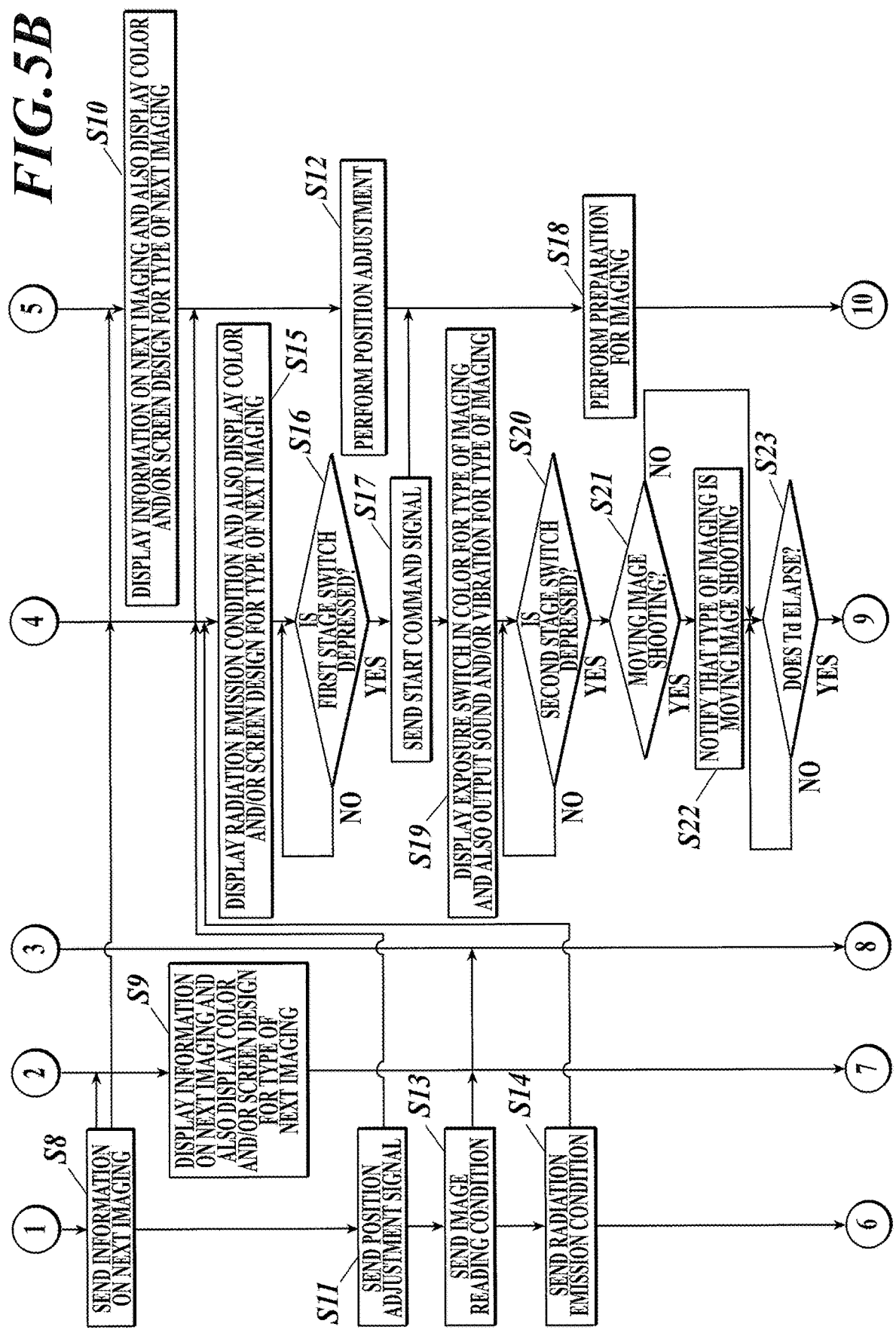

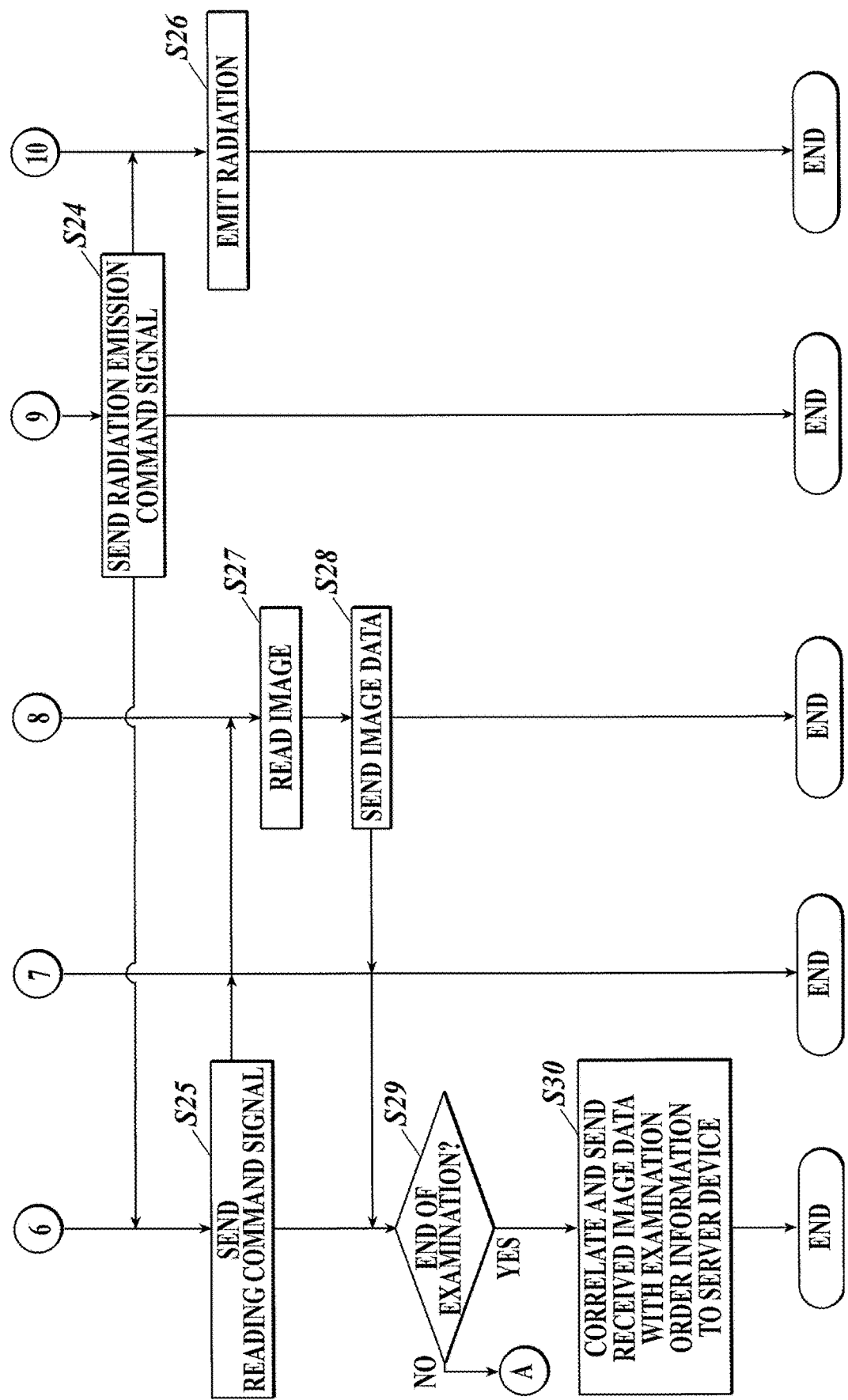

FIG.6

| PATIENT ID | NAME | SEX | BIRTHDAY | IMAGING SITE | NUMBER OF TAKEN IMAGES | NUMBER OF IMAGES TO BE TAKEN | STATE | EXAMINATION DESCRIPTION | AGE | REQUESTING DEPARTMENT | WARD | NAME IN ROMAJI | NAME IN KANA | RECEPTION NUMBER |
|---|---|---|---|---|---|---|---|---|---|---|---|---|---|---|
| 99007 | EMERGENCY PATIENT 007 | UNKNOWN | | CHEST A | 0 | 4 | NOT IMAGED YET | | | | | ER 007 | EMERGENCY PATIENT 007 | |
| 99006 | EMERGENCY PATIENT 006 | UNKNOWN | | SKULL A | 0 | 4 | NOT IMAGED YET | | | | | ER 006 | EMERGENCY PATIENT 006 | |
| 99005 | EMERGENCY PATIENT 005 | UNKNOWN | | SKULL A | 0 | 4 | NOT IMAGED YET | | | | | ER 005 | EMERGENCY PATIENT 005 | |
| 99004 | EMERGENCY PATIENT 004 | UNKNOWN | | SKULL A | 0 | 4 | NOT IMAGED YET | | | | | ER 004 | EMERGENCY PATIENT 004 | |
| 99003 | EMERGENCY PATIENT 003 | UNKNOWN | | SKULL A | 0 | 4 | NOT IMAGED YET | | | | | ER 003 | EMERGENCY PATIENT 003 | |

EXAMINATION INFORMATION

| PATIENT ID | 99007 | NAME IN ROMAJI | ER 007 |
| NAME IN KANJI | EMERGENCY PATIENT 007 | NAME IN KANA | EMERGENCY PATIENT 007 |
| BIRTHDAY | | AGE | |
| SEX | UNKNOWN | COMMENTS ON PATIENT | |

RADIATION IMAGING SYSTEM

CROSS-REFERENCE TO RELATED APPLICATIONS

The present application is a continuation application of U.S. patent application Ser. No. 15/228,416, filed on Aug. 4, 2016, the entire contents of which are incorporated herein by reference and priority to which is hereby claimed. Application Ser. No. 15/228,416 claims priority to Japanese Patent Application No. 2015-156645 filed on Aug. 7, 2015, the entire disclosure of which, including the specification, claims, drawings and abstract, is incorporated herein by reference in its entirety.

FIELD OF THE INVENTION

The present invention relates to a radiation imaging system.

DESCRIPTION OF THE RELATED ART

There have been proposed various techniques to prevent wrong imaging from happening at medical facilities where both still image shooting and moving image shooting of subjects with radiation are available.

There is described, for example, in Japanese Patent Application Publication No. 2012-110451: determining whether a portable FPD mounted on a Bucky device is a type usable for moving image shooting, based on ID information on the FPD sent from the Bucky device; determining whether imaging can be performed, based on a relationship between the type of the FPD and imaging order information; and displaying the determination result.

By the way, at the medical facilities where both still image shooting and moving image shooting of subjects with radiation are available, photographers need to know whether imaging to be performed is still image shooting or moving image shooting. So far, photographers have confirmed types of imaging, taking text information written on the screen of a console, an operation console or the like as a clue. However, immediately before imaging, photographers fix their eyes on patients. Therefore, it is not easy for photographers to confirm types of imaging by reading every word on the screen or the like. If a photographer performs imaging of a patient while wrongly recognizing the imaging type, re-imaging of the patient will become necessary. This means that the patient has been exposed to radiation meaninglessly.

BRIEF SUMMARY OF THE INVENTION

Objects of the present invention include preventing wrong imaging from happening at medical facilities where both still image shooting and moving image shooting are available.

In order to achieve at least one of the objects, according to an aspect of the present invention, there is provided a radiation imaging system including: a radiation source for still image shooting and moving image shooting performed by the radiation imaging system to obtain image data of a subject; and a notifying unit which notifies whether a type of imaging to be performed is the still image shooting or the moving image shooting in a mode in which the type is instinctively recognizable by at least one of sense of sight, sense of hearing, and sense of touch.

BRIEF DESCRIPTION OF THE SEVERAL VIEWS OF THE DRAWING

The present invention is fully understood from the detailed description given hereinafter and the accompanying drawings, which are given by way of illustration only and thus are not intended to limit the present invention, wherein:

FIG. 5A is a flowchart of an examination conducting process A performed by the radiation imaging system according to the first embodiment;

FIG. 5B is a flowchart of the examination conducting process A performed by the radiation imaging system according to the first embodiment;

FIG. 5C is a flowchart of the examination conducting process A performed by the radiation imaging system according to the first embodiment;

FIG. 6 shows an example of an examination list screen;

DETAILED DESCRIPTION OF THE INVENTION

Hereinafter, embodiments of radiation imaging systems of the present invention are described with reference to the drawings. However, the present invention is not limited thereto.

First Embodiment

[Configuration of Radiation Imaging System]

First, the configuration of a radiation imaging system 100 according to a first embodiment of the present invention is described.

Figure 1:
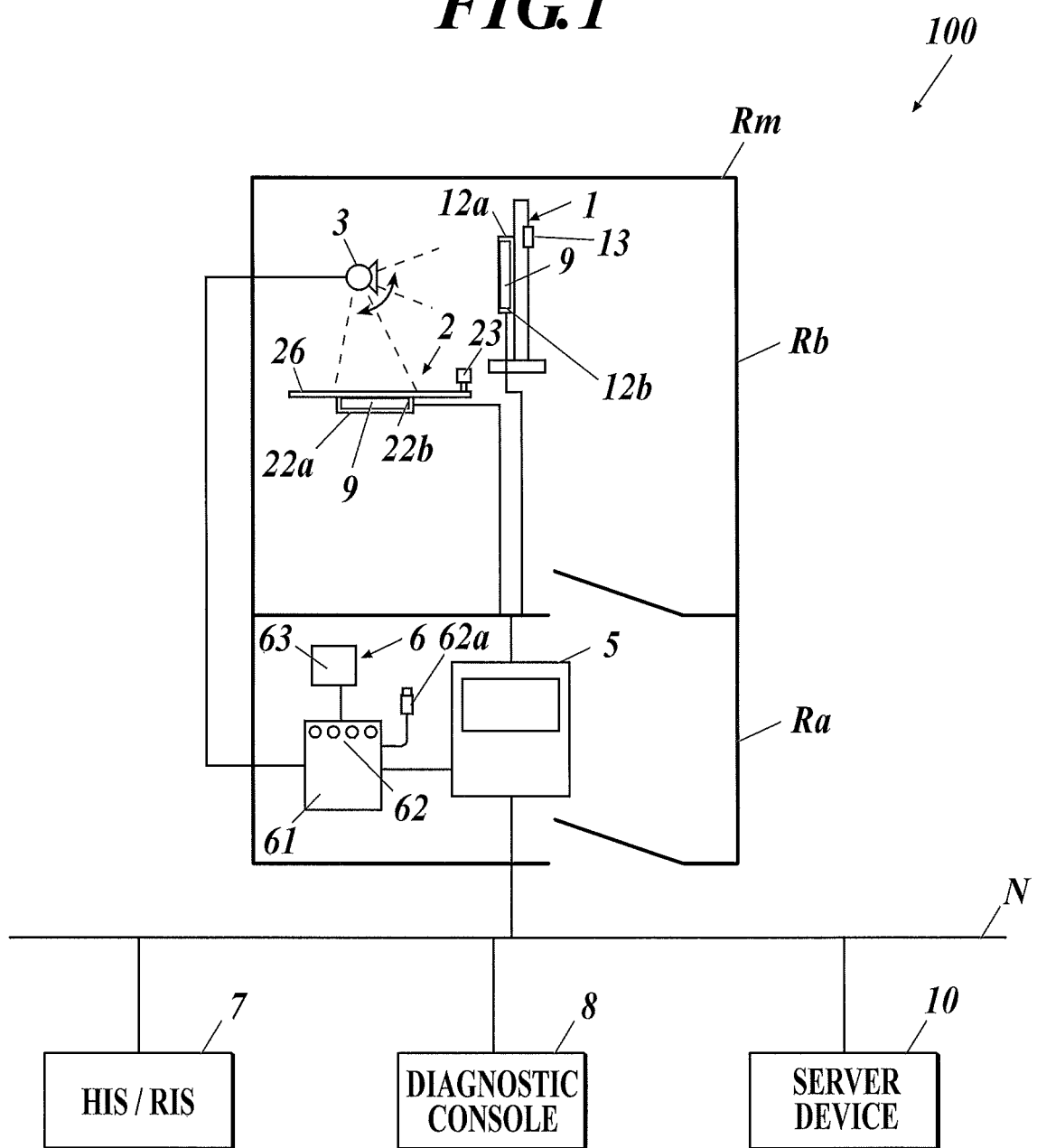
FIG. 1 shows the overall configuration of a radiation imaging system according to a first embodiment of the present invention.

FIG. 1 shows an example of the overall configuration of the radiation imaging system 100 according to the first embodiment. FIG. 1 shows the radiation imaging system 100 built in an imaging room Rm.

The radiation imaging system 100 is a system which emits radiation and can perform both still image shooting and moving image shooting of diagnosis target sites of human bodies as subjects. Still image shooting means obtaining one image of a subject in response to one imaging operation (depression of an exposure switch 62a), whereas moving image shooting is a counterpart of still image shooting and means continuously obtaining images of a subject, thereby obtaining a moving image, in response to one imaging operation. No limitations are placed on real-time characteristics of display of the images (moving image) obtained by moving image shooting and on the imaging time. Moving image shooting includes dynamic imaging and tomosynthesis imaging.

The imaging room Rm is provided with, for example, a Bucky device 1 for imaging in the upright position (upright imaging), a Bucky device 2 for imaging in the decubitus position (decubitus imaging), a radiation source 3, an imaging console 5 and an operation console 6. The imaging room Rm has a front room Ra and an imaging performing room Rb, and the imaging console 5 and the operation console 6 are disposed in the front room Ra so that a photographer, such as a radiologist, can protect himself/herself from being exposed to radiation.

Hereinafter, the devices and so forth disposed in the imaging room Rm are described.

The Bucky device 1 is a device which performs upright imaging, holding an FPD (Flat Panel Detector) 9. The Bucky device 1 includes: a holding unit 12a which holds the FPD 9; and a connector 12b which connects with a connector of the FPD 9 mounted on the holding unit 12a. The connector 12b sends/receives data to/from the FPD 9 mounted on the holding unit 12a and also supplies power to the FPD 9. The Bucky device 1 further includes: an interface to send/receive data to/from external devices, such as the imaging console 5, via a communication cable; and a foot switch which moves the holding unit 12a in the vertical direction and/or the horizontal direction. The Bucky device 1 further includes a display unit 13 which displays information on imaging (patient information on a patient as a subject, an imaging site, etc.) to be performed next.

The Bucky device 2 is a device which performs decubitus imaging, holding an FPD 9. The Bucky device 2 includes: a holding unit 22a which holds the FPD 9; and a connector 22b which connects with a connector of the FPD 9 mounted on the holding unit 22a. The connector 22b sends/receives data to/from the FPD 9 mounted on the holding unit 22a and also supplies power to the FPD 9. The Bucky device 2 further includes: an interface to send/receive data to/from external devices, such as the imaging console 5, via a communication cable; and a subject table 26 where a subject is placed. The Bucky device 2 further includes a display unit 23 which displays information on imaging (patient information on a patient as a subject, an imaging site, etc.) to be performed next.

The radiation source 3, for example, hangs from the ceiling of the imaging room Rm, and is adjusted with a not-shown drive mechanism so as to be at a predetermined position and face a predetermined direction at the time of imaging, based on a command from the imaging console 5. By changing the radiation emission direction, the radiation source 3 can emit radiation (X-rays) to the FPD 9 mounted on the Bucky device 1 for upright imaging or to the FPD 9 mounted on the Bucky device 2 for decubitus imaging. The radiation source 3 emits radiation in response to a radiation emission command from the operation console 6 and performs still image shooting or moving image shooting.

Figure 2:
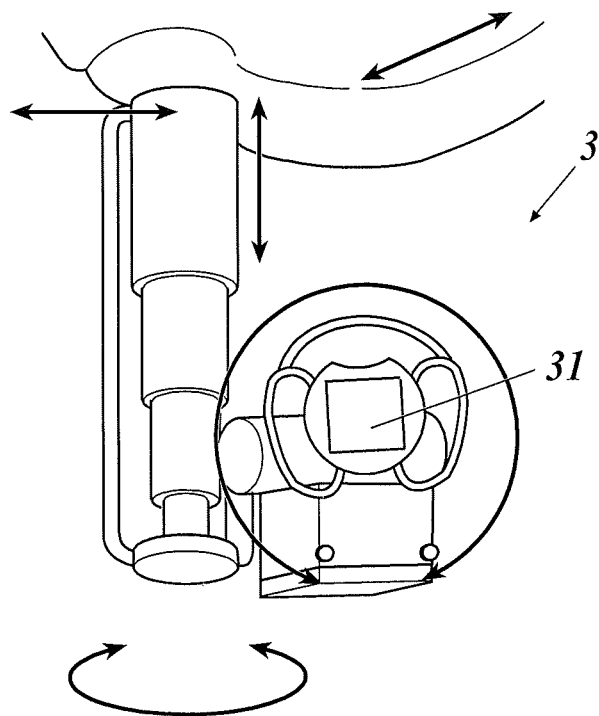
FIG. 2 is a perspective view showing details of a radiation source.

In the embodiment, as shown in FIG. 2, the radiation source 3 includes a display unit 31 which displays information on imaging (patient information on a patient as a subject, an imaging site, an imaging direction, etc.) to be performed next. FIG. 2 is a perspective view showing details of the radiation source 3.

The imaging console 5 is a device which controls imaging by controlling the units (devices) and so forth of the radiation imaging system 100. The imaging console 5 is connected to an HIS/RIS (Hospital Information System/Radiology Information System) 7, a server device 10 and so forth via a communication network N, such as a LAN (Local Area Network), and controls, based on examination order information sent from the HIS/RIS 7, the units and so forth of the radiation imaging system 100 for imaging.

Figure 3:
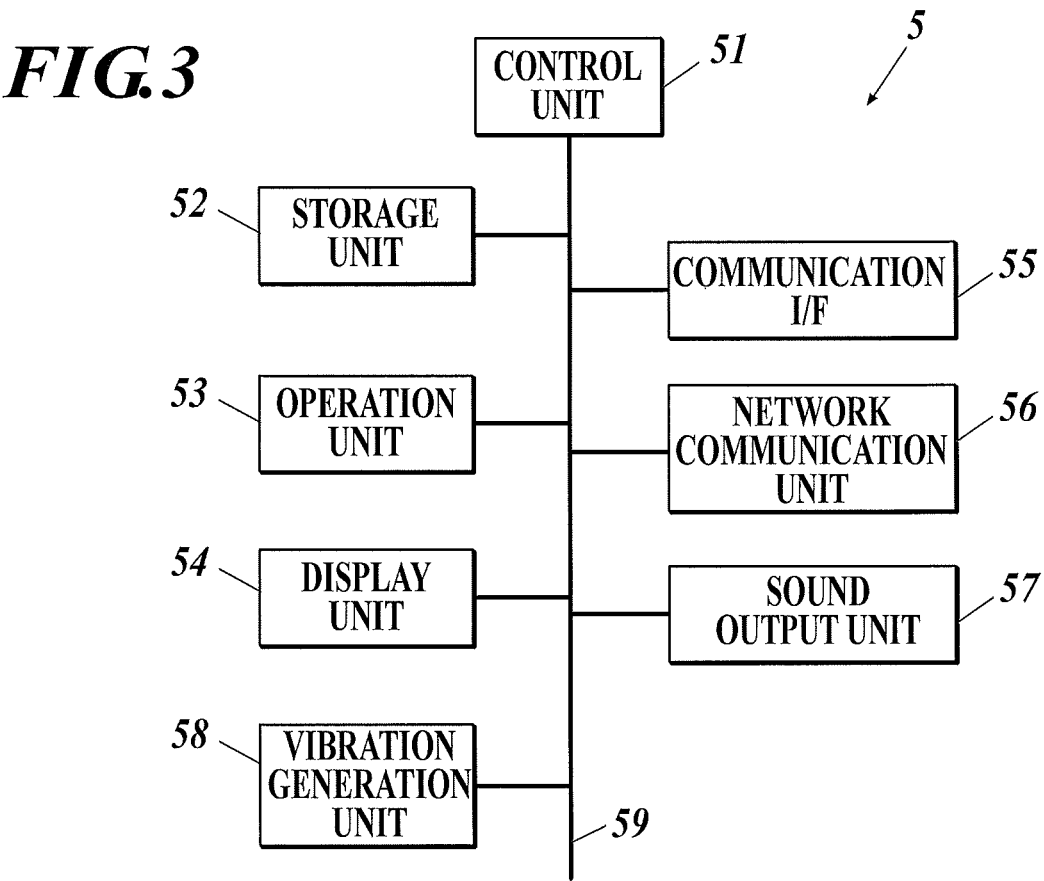
FIG. 3 shows an example of the configuration of the main part of an imaging console.

FIG. 3 shows an example of the configuration of the main part of the imaging console 5. As shown in FIG. 3, the imaging console 5 includes a control unit 51, a storage unit 52, an operation unit 53, a display unit 54, a communication I/F 55, a network communication unit 56, a sound output unit 57 and a vibration generation unit 58. These units and so forth are connected to one another via a bus 59.

The control unit 51 includes a CPU and a RAM. The CPU of the control unit 51 reads a system program and various programs, such as process programs, stored in the storage unit 52, opens the read programs on the RAM and performs various processes in accordance with the opened programs.

For example, the control unit 51 sends a request to the HIS/RIS 7 via the network communication unit 56 at predetermined time intervals so as to obtain examination order information newly registered in the HIS/RIS 7.

Further, for example, the control unit 51 controls the units and so forth of the radiation imaging system 100 by performing steps on the imaging console 5 side of an examination conducting process A shown in FIG. 5A to FIG. 5C for notification of the type of imaging (imaging type) and for imaging.

The storage unit 52 is constituted of an HDD (Hard Disk Drive), a nonvolatile semiconductor memory or the like.

The storage unit 52 stores therein various programs and data. For example, the storage unit 52 stores therein a program to perform the steps on the imaging console 5 side of the examination conducting process A shown in FIG. 5A to FIG. 5C.

The storage unit 52 also stores therein imaging conditions (radiation emission conditions and image reading conditions) correlated with respective combinations of imaging types and imaging sites. The radiation emission conditions include a value of current of an X-ray tube, a value of voltage of the X-ray tube, a filter type, SID (Source to Image-receptor Distance), a pulse rate, a pulse width and a pulse interval in moving image shooting. The image reading conditions include a pixel size, an image size (matrix size), a frame rate and a frame interval in moving image shooting. The frame rate matches the pulse rate.

The storage unit 52 also stores therein examination order information sent from the HIS/RIS 7 at predetermined time intervals. The examination order information includes: examination identification information (an examination ID, etc.); an examination date; patient information on a patient as a subject, such as a name of the patient; and information on each imaging (an imaging ID, an imaging site, an imaging direction, a body position (upright position or decubitus position), an imaging type (still image shooting or moving image shooting), etc.) to be performed in an examination.

The operation unit 53 includes: a keyboard including letter input keys, number input keys and various function keys; and a pointing device, such as a mouse, and outputs depression signals of depressed keys of the keyboard and operation signals of the mouse to the control unit 51 as input signals.

The display unit 54 is constituted of a monitor, such as a CRT (Cathode Ray Tube) or an LCD (Liquid Crystal Display), and displays various screens in response to commands of display signals input from the control unit 51.

The screen of the display unit 54 may be provided with a pressure sensitive (resistive) touch panel (not shown) formed thereon in which transparent electrodes are arranged to be grid-like, thereby being a touchscreen constituted of the display unit 54 integrated with the operation unit 53. In this case, the touch panel detects XY coordinates of a stress point depressed with a finger, a touch pen or the like in the form of a voltage value, and outputs the detected position signal to the control unit 51 as an operation signal. The display unit 54 may be higher-definition than a monitor used in a general PC (Personal Computer).

The communication I/F 55 is an interface to connect with and send/receive data to/from the Bucky device 1, the Bucky device 2 and the operation console 6.

The network communication unit 56 is constituted of a network interface or the like and sends/receives data to/from external devices connected to the communication network N via a switching hub.

The sound output unit 57 includes a speaker and outputs sounds (voices) under the control of the control unit 51.

The vibration generation unit 58 generates and outputs vibrations under the control of the control unit 51.

The operation console 6 is a terminal which includes a control unit 61, an operation unit 62 including an exposure switch 62a, a display unit 63 and a communication I/F (not shown) and controls radiation emission of the radiation source 3. The operation console 6 sends, to the radiation source 3, position adjustment command signals sent from the imaging console 5; displays, on the display unit 63, radiation emission conditions sent from the imaging console 5; adjusts the radiation emission conditions with operations of a photographer, such as a radiologist, according to, for example, body thickness of a subject; and sends start command signals and radiation emission command signals to the radiation source 3 in response to depression of the exposure switch 62a, for example.

Figure 4:
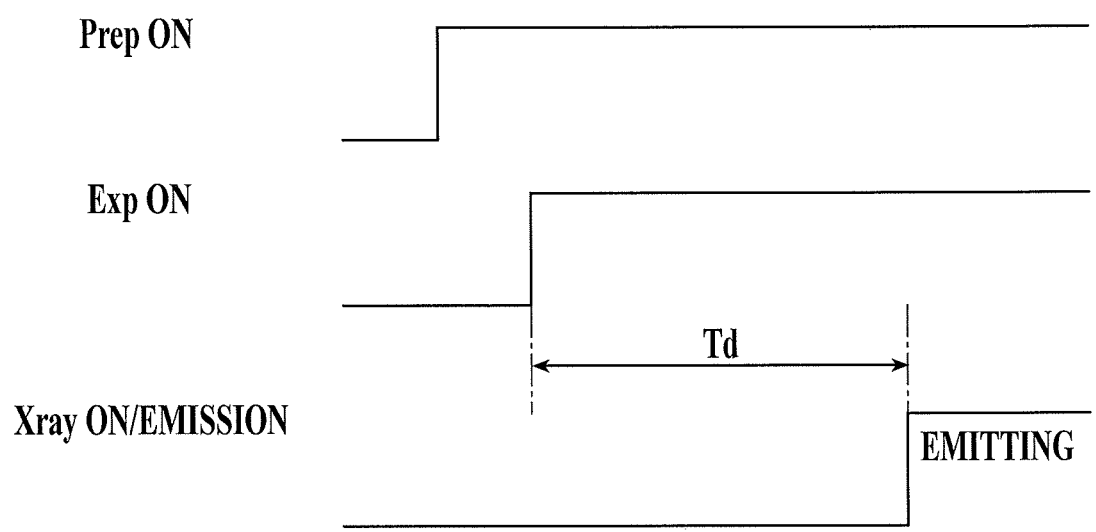
FIG. 4 shows a relationship between depression of an exposure switch and radiation emission.

The exposure switch 62a is, as shown in FIG. 4, a two-stage switch. When the first stage switch is depressed (Prep ON), a start command signal is input to the radiation source 3, and when the second stage switch is depressed (Exp ON), after a delay time Td elapses, a radiation emission command signal is input (Xray ON) to the radiation source 3. The exposure switch 62a is provided with an LED (Light-Emitting Diode) or the like, whereby the display color thereof can be changed. The exposure switch 62a is further provided with not-shown sound output unit and vibration generation unit to respectively output sounds and vibrations in response to depression of the first stage switch and the second stage switch. Details thereof are described below.

The HIS/RIS 7 generates examination order information with registration operations of an operator. The examination order information includes: patient information on a patient as a subject, such as the name, sex, age, height and weight of the patient; information on each imaging (the imaging ID, imaging site, imaging direction, body position (upright position or decubitus position), imaging type (still image shooting or moving image shooting), imaging method, etc. of each imaging) to be performed in an examination. The examination order information is not limited to the above, and hence may further include other information or may include only some of the above.

The diagnostic console 8 is a computer device which obtains medical images from the server device 10 and displays the obtained medical images so that a doctor can perform radiographic interpretation and make diagnosis.

The FPD 9 is a radiation detector which includes a control unit, a detection unit, a storage unit, a connector and a battery.

The detection unit of the FPD 9 is constituted of detection elements arranged two-dimensionally at predetermined points on a substrate, such as a glass substrate. The detection elements detect radiation (intensity of radiation) emitted from the radiation source 3 and passing through at least a subject, convert the detected radiation into electric signals, and accumulate the electric signals therein. The detection elements are constituted of photodiodes or the like of a semiconductor image sensor. The detection elements are connected to TFTs (Thin Film Transistors) or the like which constitute a switching unit. The switching unit controls accumulation and reading of the electric signals.

The control unit of the FPD 9 controls the switching unit of the detection unit based on image reading conditions input from the imaging console 5 via the Bucky device 1 or 2 to switch the radiation detection elements ("detection elements" hereinafter) to read the electric signals accumulated in the detection elements, thereby generating image data. The control unit of the FPD 9 outputs the generated image data to the imaging console 5 via the connector and the Bucky device 1 or 2.

The connector of the FPD 9 connects with the connector (12b or 22b) of the Bucky device 1 or 2 and sends/receives data to/from the Bucky device 1 or 2. The connector of the FPD 9 supplies power supplied from the connector of the Bucky device 1 or 2 to the functional units. The connector of the FPD 9 may be configured to charge the battery.

The server device 10 has a database where image data of medical images sent from the imaging console 5 are correlated and stored with examination order information. The server device 10 reads the medical images from the database and sends the read medical images to the diagnostic console 8 as requested.

(Imaging Action)

Next, flow of an examination conducting process performed by the radiation imaging system 100 is described.

FIG. 5A to FIG. 5C show the flow of an examination conducting process A performed by the radiation imaging system 100. In the examination conducting process A, the display unit 54, the sound output unit 57 and the vibration generation unit 58 of the imaging console 5, the display unit 13 of the Bucky device 1, the display unit 23 of the Bucky device 2, the display unit 31 of the radiation source 3 and the exposure switch 62a of the operation console 6 function as a notifying unit which notifies whether the type of imaging to be performed in an examination is still image shooting or moving image shooting in a mode in which the type of imaging is instinctively recognizable by the sense of sight, the sense of hearing and/or the sense of touch, without text information being read.

First, the control unit 51 of the imaging console 5 determines whether each ordered examination contains moving image shooting based on its examination order information stored in the storage unit 52, and causes the display unit 54 to display an examination list screen 541 where examination order information on an examination containing moving image shooting and examination order information on an examination not containing moving image shooting are displayed in different colors (Step S1).

FIG. 6 shows an example of the examination list screen 541. As shown in FIG. 6, the examination list screen 541 is provided with an examination list display section 541a where a list of examination order information on examinations is displayed, an examination information display section 541b where examination order information selected with the operation unit 53 is displayed, an examination start button 541c to instruct start of examination, and so forth. In the embodiment, as shown in FIG. 6, in the list of examination order information on examinations displayed in the examination list display section 541a, examination order information on an examination containing moving image shooting and examination order information on an examination not containing moving image shooting (i.e., rows thereof) are displayed in different background colors. Alternatively, these examination order information (texts) themselves may be displayed in different colors (i.e., text colors). Thereby, before start of an examination(s), a photographer can instinctively recognize an examination(s) containing moving image shooting, without reading a text(s).

In the following explanation, whenever examination order information or information on each imaging is displayed in a color for the type(s) of imaging, the information itself may be displayed in a color for the type(s) of imaging, or the background of the information in the row may be displayed in a color for the type(s) of imaging.

The control unit 51 waits until, with the operation unit 53, examination order information on an examination to be conducted next is selected on the examination list screen 541 and the examination start button 541c is depressed (Step S2; NO, Step S3; NO).

When, with the operation unit 53, examination order information on an examination is selected on the examination list screen 541 (Step S2; YES) and the examination start button 541c is depressed (Step S3; YES), the control unit 51 determines whether the started examination contains moving image shooting based on the examination order information on the started examination (Step S4).

When determines that the started examination contains moving image shooting (Step S4; YES), the control unit 51 causes the sound output unit 57 to output a predetermined sound which indicates that an examination contains moving image shooting (Step S5) and proceeds to Step S6. Examples of the predetermined sound include: a predetermined buzzer sound; "It contains moving image shooting" or the like with a voice; and a predetermined sound effect. Thus, if an examination contains moving image shooting, at the timing of start of the examination, this is notified using a sound. Hence, a photographer can instinctively recognize that the started examination contains moving image shooting.

On the other hand, when determines that the started examination does not contain moving image shooting (Step S4; NO), the control unit 51 proceeds to Step S6.

At Step S6, the control unit 51 causes the display unit 54 to display an examination screen 542 where information on each imaging contained in the started examination (i.e., current examination) is displayed in a color for the type of imaging and/or with an icon for the type of imaging (Step S6).

Figure 7:
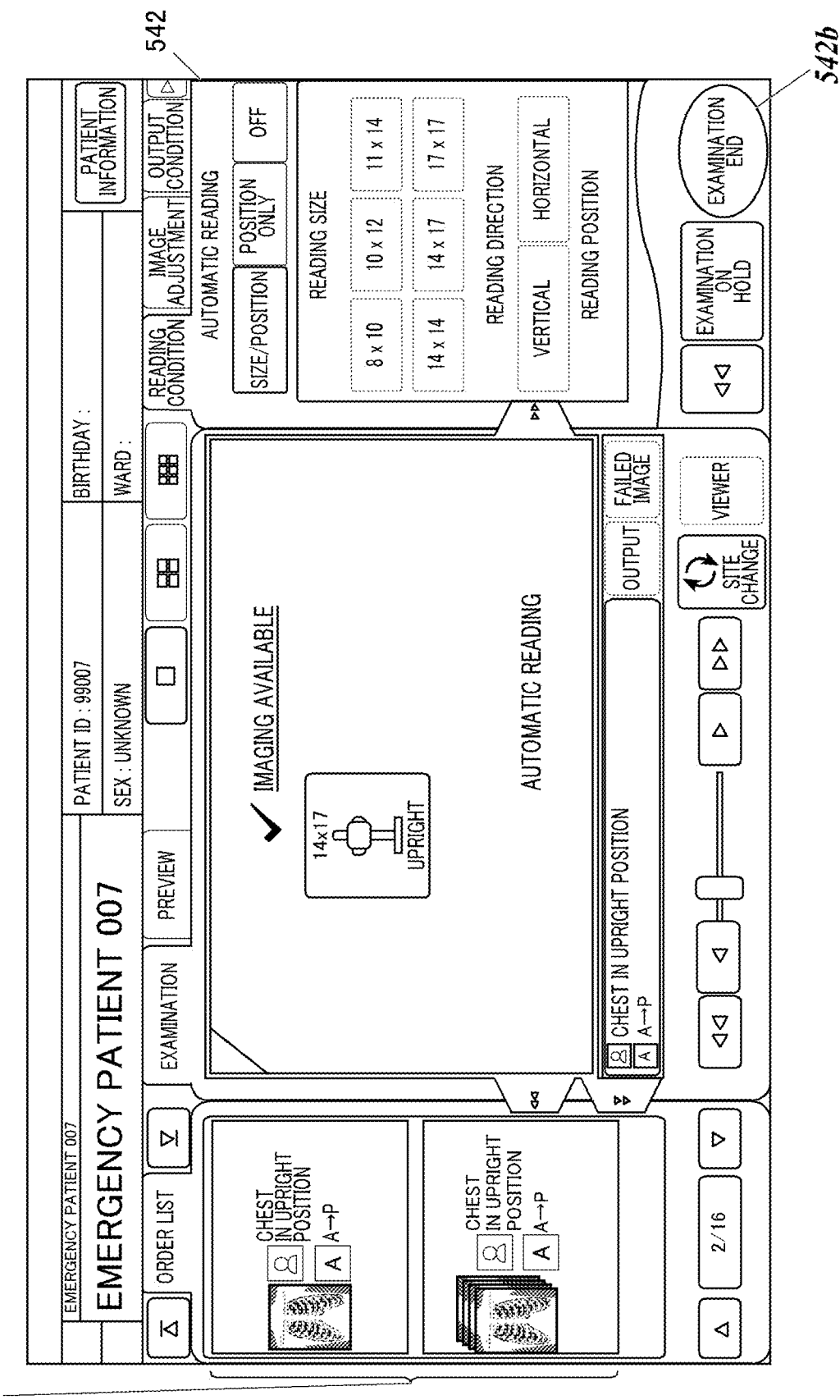
FIG. 7 shows an example of an examination screen.

FIG. 7 shows an example of the examination screen 542. As shown in FIG. 7, on the examination screen 542, imaging selection buttons 542a are displayed. On each imaging selection button 542a, information on one imaging (e.g., an imaging site, a body position, an imaging direction, etc.) contained in the current examination is displayed. The imaging selection buttons 542a are displayed in different colors (text colors or background colors) and with different screen designs (e.g., icons) for their respective types of imaging being still image shooting or moving image shooting. When an imaging selection button 542a is selected with the operation unit 53, imaging correlated with the selected button 542a is recognized as imaging to be performed next. Thus, the imaging selection buttons 542a are displayed in colors and/or with icons according to whether the types of imaging in the current examination are each still image shooting or moving image shooting. Hence, a photographer can instinctively recognize whether imaging to select is still image shooting or moving image shooting, without reading a text.

Next, the control unit 51 waits until one of the imaging selection buttons 542a is depressed with the operation unit 53 (Step S7).

When one of the imaging selection buttons 542a is depressed (i.e., imaging to be performed next is selected) with the operation unit 53 (Step S7; YES), the control unit 51 sends information on the selected imaging (patient information, an imaging type, an imaging site, an imaging direction, etc.) and a display control signal to the radiation source 3 and the Bucky device 1 or 2 suitable for the body position information on the selected imaging (the next imaging) (Step S8).

When receives the information on the next imaging and the display control signal from the imaging console 5, the radiation source 3 and the Bucky device 1 or 2 cause their display units (the display unit 31 and the display unit 13 or 23) to display the information on the next imaging, and also cause their display units (the display unit 31 and the display unit 13 or 23) to display a color and/or a screen design for the type of the next imaging (Step S9 and Step S10)

The control unit 51 also sends a position adjustment signal for the body position information on the selected imaging (the next imaging) to the radiation source 3 (Step S11). The radiation source 3 performs position adjustment based on the received position adjustment signal (Step S12).

The control unit 51 also sends, via the Bucky device (1 or 2) suitable for the body position information on the selected imaging (the next imaging), image reading conditions for the imaging site and the imaging type to the FPD 9 to cause the FPD 9 to prepare for imaging, such as resetting (Step S13), and also sends the imaging type and radiation emission conditions for the imaging site and the imaging type to the operation console 6 (Step S14).

In the operation console 6, when receives the radiation emission conditions from the imaging console 5, the control unit 61 causes the display unit 63 to display the radiation emission conditions, and also causes the display unit 63 to display a color and/or a screen design for the type of the next imaging (Step S15). Further, the control unit 61 adjusts the radiation emission conditions in response to input from the operation unit 62 and sets the adjusted radiation emission conditions in the radiation source 3.

As to a photographer, once selects the imaging to be performed next (the next imaging) from the examination screen 542 of the imaging console 5 in the front room Ra, the photographer moves to the imaging performing room Rb, and positions the patient, adjusts the position and direction of the radiation source 3, and gives the patient guidance on the imaging, for example. At the time, the display unit 13 or 23 of the Bucky device 1 or 2 and the display unit 31 of the radiation source 3 in the imaging performing room Rb display a color and/or a screen design for the type of the next imaging. Hence, a photographer can instinctively recognize and check, in the imaging performing room Rb, whether the next imaging is still image shooting or moving image shooting without reading a text. This can prevent a situation where a photographer forgets to check the imaging type from happening, and accordingly the photographer can give a patient guidance on imaging suitable for the imaging type. For example, a photographer can give a patient guidance by saying, for example, "Stop breathing with a cue." in the case of still image shooting or "Imaging takes ** seconds. Breathe comfortably." in the case of moving image shooting. When completes preparation for imaging, the photographer depresses the exposure switch 62a of the operation console 6.

In the operation console 6, the control unit 61 waits until the first stage switch of the exposure switch 62a is depressed. When the first stage switch thereof is depressed (Step S16; YES), the control unit 61 sends a start command signal to the radiation source 3 (Step S17). The radiation source 3 prepares for imaging, for example, rotates the rotating anode (Step S18). The control unit 61 causes the exposure switch 62a to display a color for the type of the next imaging, and also causes the exposure switch 62a to output a sound and/or a vibration for the type of the next imaging (Step S19). For example, the control unit 61 causes the exposure switch 62a to output a sound which indicates that the first stage switch is depressed using a sound of a frequency for the type of the next imaging. Further, the control unit 61 causes the exposure switch 62a to output a vibration only when the type of the next imaging is moving image shooting.

Next, the control unit 61 waits until the second stage switch of the exposure switch 62a is depressed. When the second stage switch thereof is depressed (Step S20; YES), the control unit 61 determines whether the type of the next imaging is moving image shooting (Step S21). When determines that the type of the next imaging is moving image shooting (Step S21; YES), the control unit 61 causes the sound output unit of the exposure switch 62a to output a sound to notify the photographer that the type of the next imaging is moving image shooting (Step S22). The control unit 61 waits a delay time Td suitable for the imaging type from the time the second stage switch of the exposure switch 62a is depressed (Step S23).

When the delay time Td elapses (Step S23; YES), the control unit 61 sends a radiation emission command signal to the radiation source 3 and the imaging console 5 (Step S24). The imaging console 5 sends a reading command signal to the FPD 9 via the Bucky device (1 or 2) (Step S25). The radiation source 3 starts emitting radiation, thereby emitting radiation according to the radiation emission conditions set by the operation console 6 (Step S26). The FPD 9 reads an image(s) according to the image reading conditions (Step S27) and sends the obtained image data to the imaging console 5 via the Bucky device (1 or 2) (Step S28).

At the timing when radiation emission is started in response to depression of the exposure switch 62a, the photographer is notified about the imaging type with the sound, vibration, color, radiation emission delay time, and/or the like. This can prevent the photographer from performing wrong imaging (the wrong imaging means, for example: performing still image shooting instead of moving image shooting by mistake; and performing video imaging, in which breathing should not be stopped, by giving a patient guidance by saying "Stop breathing."), and accordingly can prevent the patient from being exposed to radiation meaninglessly.

When the imaging finishes, the control unit 51 of the imaging console 5 determines whether it is instructed to end the examination with the operation unit 53. When determines that it is not instructed to end the examination (Step S29; NO), the control unit 51 returns to Step S7. On the other hand, when determines that it is instructed to end the examination (Step S29; YES), the control unit 51 correlates and sends the received image data with the examination order information to the server device 10 (Step S30) and ends the examination.

Second Embodiment

Next, a second embodiment of the present invention is described.

First, the configuration of a radiation imaging system according to the second embodiment of the present invention is described.

Figure 8:
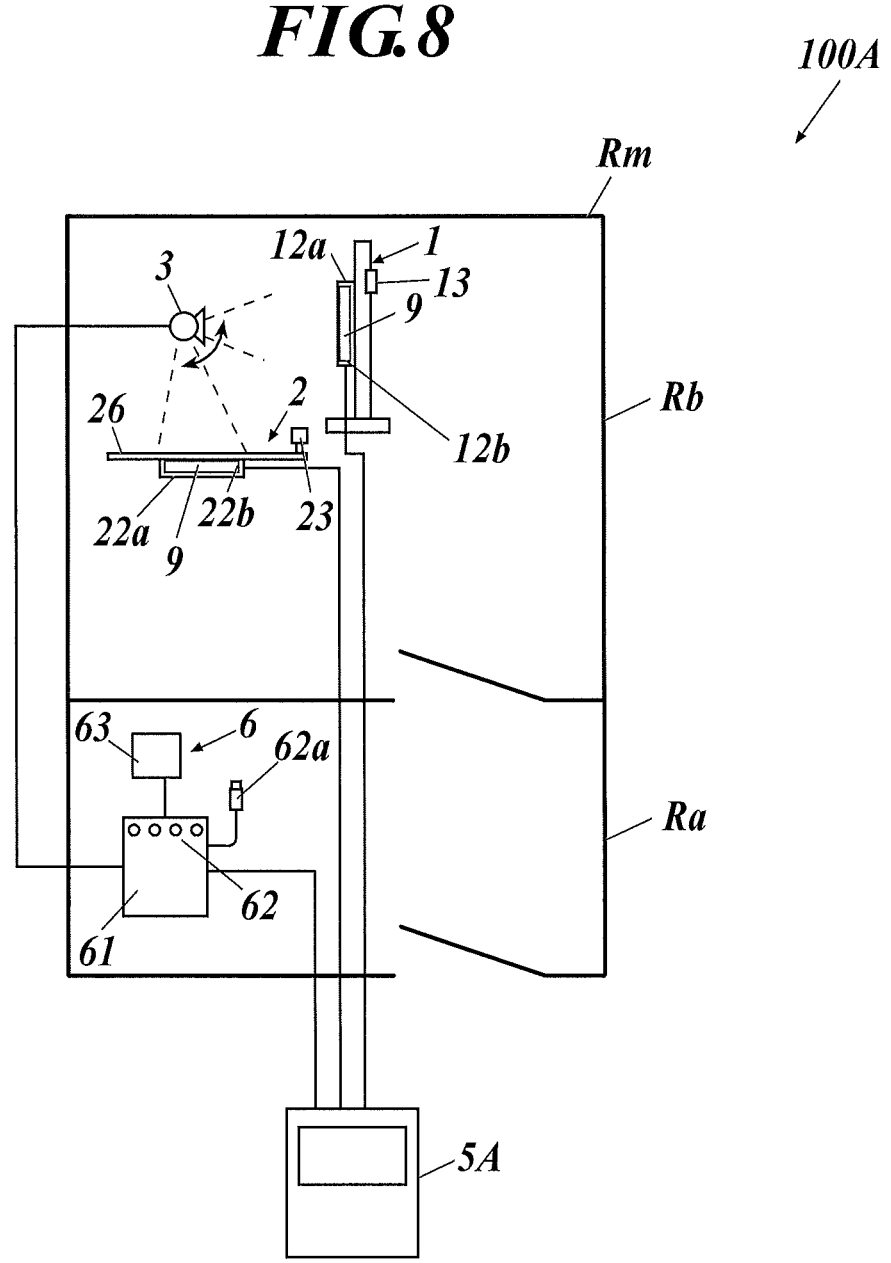
FIG. 8 shows the overall configuration of a radiation imaging system according to a second embodiment of the present invention.

FIG. 8 shows an example of the overall configuration of a radiation imaging system 100A according to the second embodiment. The radiation imaging system 100A is a system built in a relatively small-size facility, such as an office in private practice or a clinic. For example, as shown in FIG. 8, the front room Ra of the imaging room Rm is provided with the operation console 6; the imaging performing room Rb is provided with the Bucky devices 1 and 2, the radiation source 3 and the FPDs 9; and a consultation room or the like outside the imaging room Rm is provided with a console 5A. The console 5A has the functions as an imaging console, a diagnostic console and a server device described in the first embodiment. The radiation imaging system 100A is not provided with a device which issues examination order information in advance, such as the HIS/RIS 7 described in the first embodiment. Instead, the console 5A is configured to select the type of each imaging in an examination to be conducted from still image shooting and moving image shooting.

The configurations of the Bucky devices 1 and 2, the radiation source 3, the operation console 6 and the FPD(s) 9 of the second embodiment are the same as those described in the first embodiment, and therefore descriptions thereof are omitted here. The functional configuration of the console 5A is the same as that shown in FIG. 3, but programs and data stored in the storage unit 52 of the console 5A are different from those stored in the storage unit 52 of the console 5. More specifically, the storage unit 52 of the console 5A stores therein programs to perform the functions as an imaging console, a diagnostic console and a server device, and the functions as an imaging console, a diagnostic console and a server device are realized by the control unit 51 working together with the programs stored in the storage unit 52. The program to perform the function as an imaging console includes a program to perform steps on the console 5A side of the examination conducting process B shown in FIG. 9A to FIG. 9C.

The storage unit 52 of the console 5A has a patient DB (DataBase) where patient information is stored, an image DB where image data obtained by imaging is stored, and so forth. Except these, the configuration of the console 5A is the same as that of the console 5 described in the first embodiment, and therefore descriptions thereof are omitted here.

Next, action of the second embodiment is described.

Figure 9A:
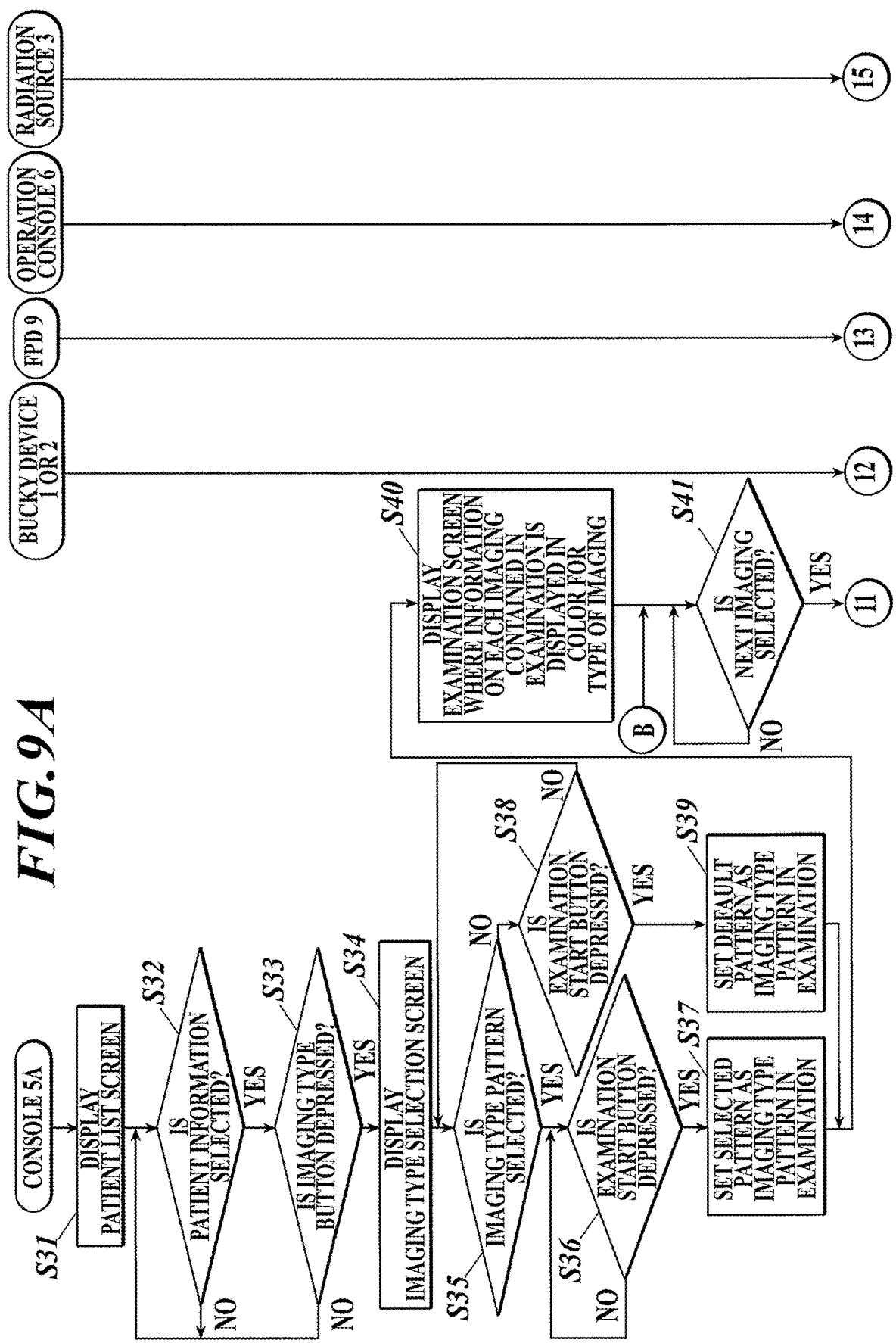
FIG. 9A is a flowchart of an examination conducting process B performed by the radiation imaging system according to the second embodiment.
Figure 9B:
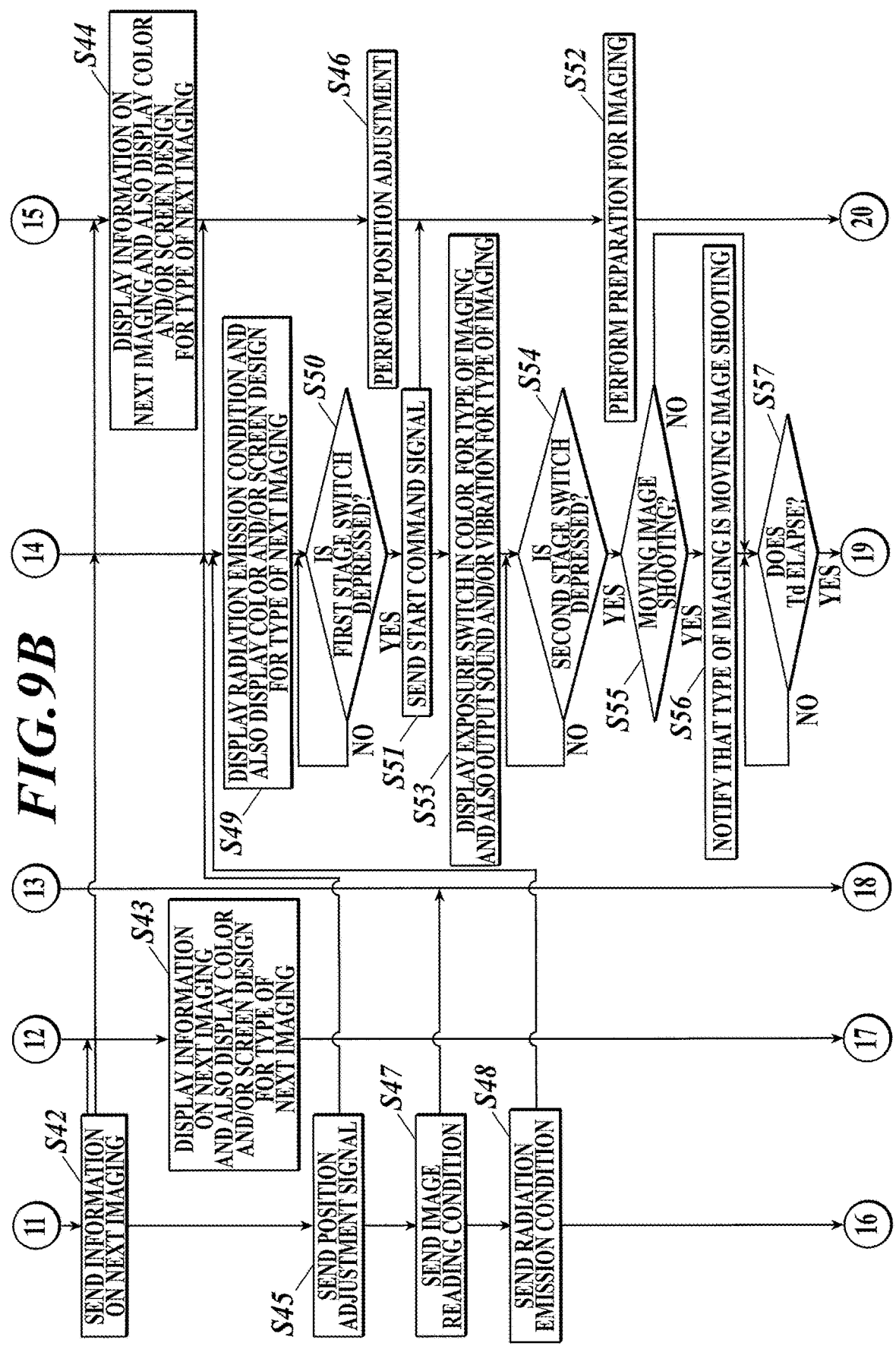
FIG. 9B is a flowchart of the examination conducting process B performed by the radiation imaging system according to the second embodiment.
Figure 9C:
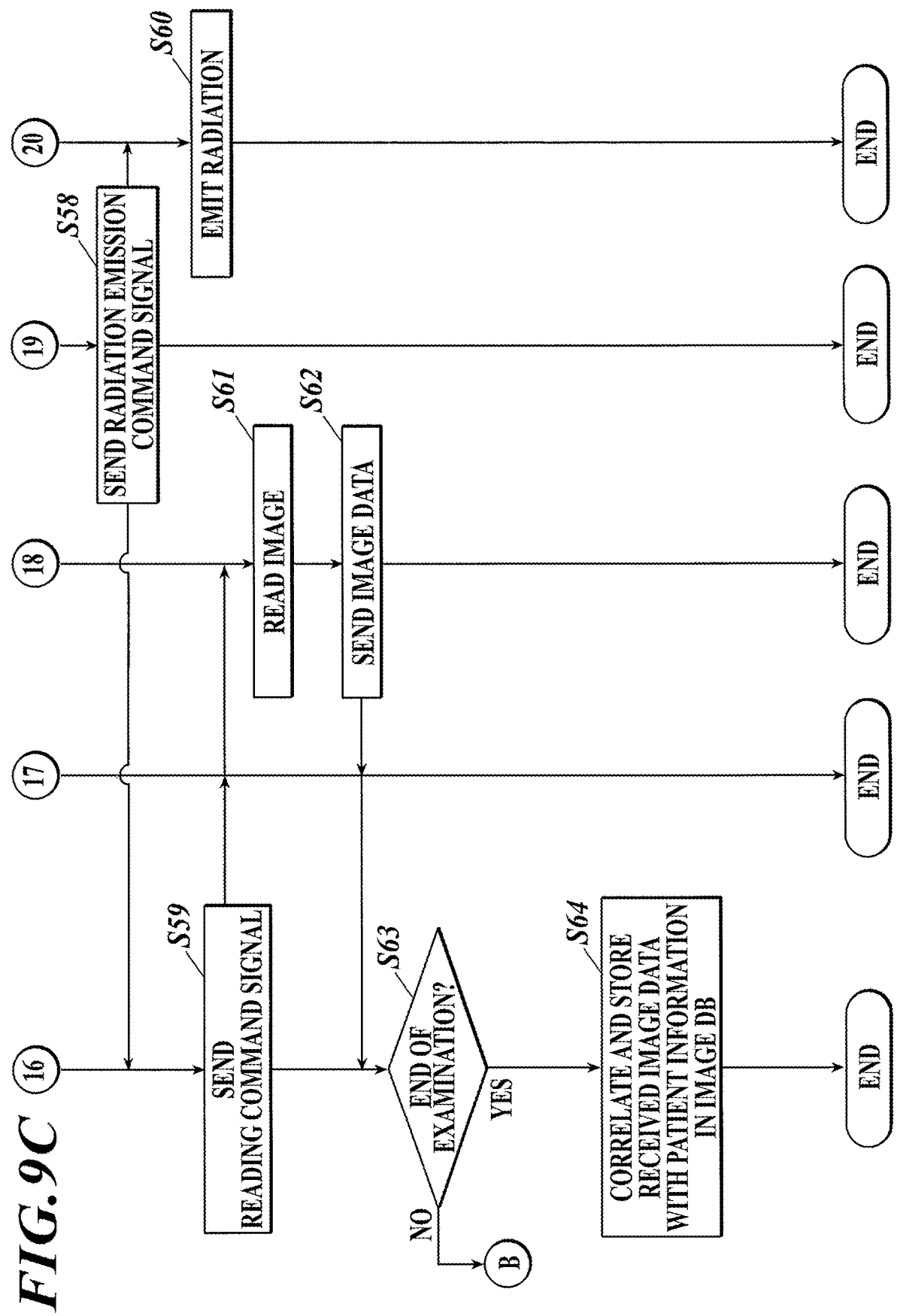
FIG. 9C is a flowchart of the examination conducting process B performed by the radiation imaging system according to the second embodiment.

FIG. 9A to FIG. 9C show flow of an examination conducting process B performed by the radiation imaging system 100A according to the second embodiment.

First, the control unit 51 of the console 5A reads patient information stored in the patient DB of the storage unit 52, and causes the display unit 54 to display a patient list screen (not shown) (Step S31).

The patient list screen is a screen where a list of patient information on patients is displayed. The patient list screen is provided with an imaging type button. When, with the operation unit 53, patient information on a patient is selected on the patient list screen and the imaging type button is depressed, an imaging type selection screen 543 (shown in FIG. 10) is displayed. The imaging type selection screen 543 is to select and input a pattern of types of imaging to be performed (i.e., an imaging type pattern) in an examination to be conducted on the selected patient.

The control unit 51 waits until, with the operation unit 53, patient information on a patient is selected on the patient list screen and the imaging type button is depressed (Step S32; NO, Step S33; NO).

When, with the operation unit 53, patient information on a patient is selected on the patient list screen (Step S32; YES) and the imaging type button is depressed (Step S33; YES), the control unit 51 causes the display unit 54 to display the imaging type selection screen 543 (Step S34).

Figure 10:
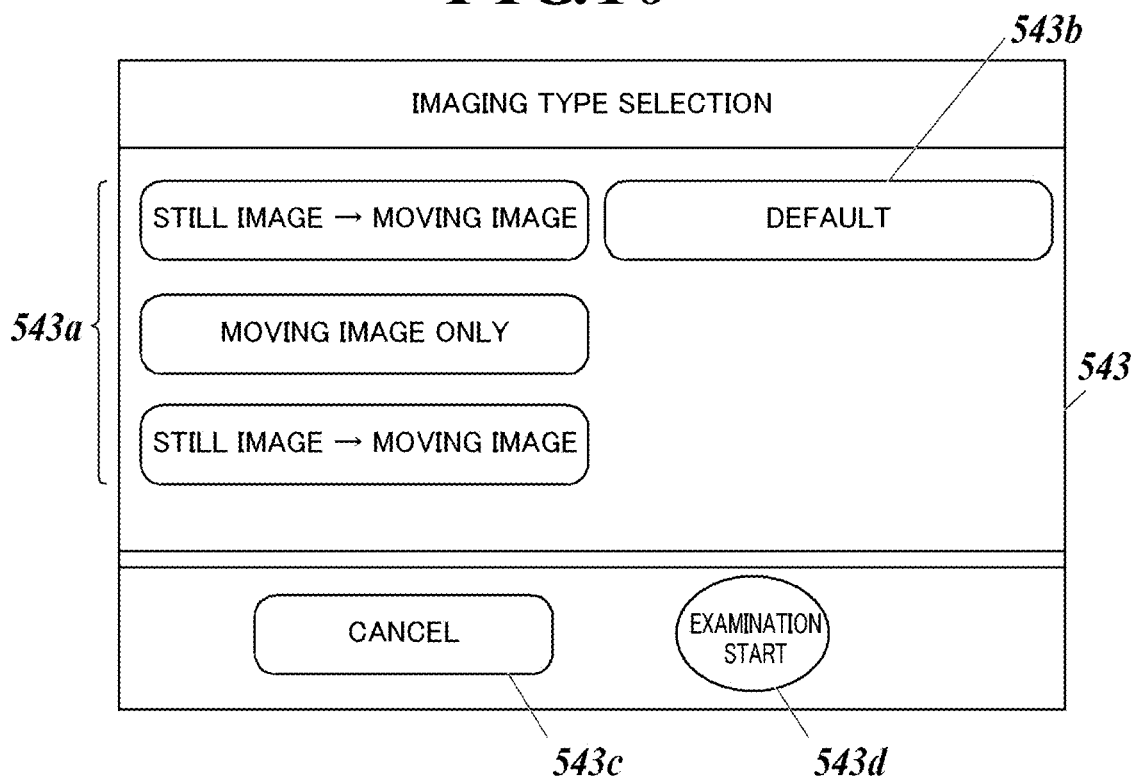
FIG. 10 shows an example of an imaging type selection screen.

FIG. 10 shows an example of the imaging type selection screen 543. As shown in FIG. 10, the imaging type selection screen 543 is provided with pattern selection buttons 543a to select an imaging type pattern (a pattern of the order of types of imaging (still image shooting or moving image shooting) to be performed) in an examination, a default button 543b, a cancel button 543c, and an examination start button 543d. The default button 543b is correlated with the most frequent imaging order pattern (e.g., still image shooting only) at a facility, and when the imaging type selection screen 543 is opened (displayed), the default button 543b is automatically selected. Hence, for the default pattern, when the examination start button 543d is depressed, the default pattern is automatically set. The pattern selection buttons 543a are respectively correlated with patterns 1 to 3 (e.g., pattern 1: still image shooting→moving image shooting, pattern 2: moving image shooting only, pattern 3: moving image shooting→still image shooting), and the imaging type pattern correlated with the depressed pattern selection button 543a is set. The patterns 1 to 3 are customizable by a user operating the operation unit 53 so as to be suitable for the management of the facility.

When one of the pattern selection buttons 543a is depressed with the operation unit 53 (Step S35; YES), the control unit 51 waits until the examination start button 543d is depressed (Step S36). When the examination start button 543d is depressed with the operation unit 53 (Step S36; YES), the control unit 51 sets the pattern correlated with the depressed pattern selection button 543a as the imaging type pattern in the started examination (Step S37) and proceeds to Step S40.

On the other hand, when, with the operation unit 53, none of the pattern selection buttons 543a is depressed (Step S35; NO) but the examination start button 543d is depressed (Step S38; YES), the control unit 51 sets the default pattern as the imaging type pattern in the started examination (Step S39) and proceeds to Step S40.

At Step S40, the control unit 51 causes the display unit 54 to display the examination screen 542 where information on each imaging (here, information indicating the type of each imaging) contained in the started examination (i.e., current examination) is displayed in a color for the type of imaging and/or with an icon for the type of imaging (Step S40). The examination screen 542 in the second embodiment is approximately the same as that shown in FIG. 7, but is configured to select a Bucky device to be used for each imaging.

Steps S41 to S62 in the second embodiment are the same as those described in the first embodiment, and therefore descriptions thereof are omitted here. At Steps S40 and S41 to S62, the display unit 54, the sound output unit 57 and the vibration generation unit 58 of the imaging console 5A, the display unit 13 of the Bucky device 1, the display unit 23 of the Bucky device 2, the display unit 31 of the radiation source 3 and the exposure switch 62a of the operation console 6 function as the notifying unit which notifies whether the type of imaging to be performed in an examination is still image shooting or moving image shooting in a mode in which the type of imaging is instinctively recognizable by the sense of sight, the sense of hearing and/or the sense of touch, without text information being read.

At Step S63, when determines that it is instructed to end the examination with the operation unit 53 (Step S63; YES), the control unit 51 correlates and stores the received image data with the patient information in the image DB of the storage unit 52 (Step S64) and ends the examination conducting process B.

In the second embodiment, as a selection unit to select a pattern of the order of types of imaging (an imaging type pattern) to be performed in an examination, the imaging type selection screen 543 is displayed on the display unit 54 of the console 5A, and an imaging type pattern in an examination can be set with a selection operation on the screen 543. Hence, even in a system which does not issue examination order information, the console 5A, and the display units 13, 23 and 31 and the exposure switch 62a disposed in the imaging room Rm, and the like can display a color and/or a screen design and output a sound and/or a vibration for the type of imaging, for example. Hence, a photographer can instinctively recognize the type of the next imaging.

As described above, the radiation imaging system 100 (100A) notifies whether the type of imaging to be performed is still image shooting or moving image shooting in a mode in which the type of imaging is instinctively recognizable by at least one of the sense of sight, the sense of hearing and the sense of touch. More specifically, the radiation imaging system 100 (100A) notifies whether the type of imaging to be performed is still image shooting or moving image shooting in the mode in which the type of imaging is instinctively recognizable, using at least one of colors, screen designs, sounds and vibrations.

This allows a photographer to instinctively recognize whether the type of imaging to be performed is still image shooting or moving image shooting without reading a text, and can prevent wrong imaging from happening.

The above embodiments are preferred examples of the present invention and thus are not intended to limit the present invention.

For example, in the embodiments, for a photographer to instinctively recognize the type of the next imaging, various forms are used; for example, a color, a screen deign, a sound and a vibration of the imaging console 5 (console 5A), the display units 13, 23 and 31, the exposure switch 62a, and so forth. However, it is unnecessary to employ all of these, and a user can customize the notifying forms.

In the above, as a computer readable medium of the programs of the present invention, an HDD, a nonvolatile semiconductor memory or the like is used. However, the computer readable medium thereof is not limited thereto. As the computer readable medium thereof, a portable storage medium, such as a CD-ROM, can be used. Further, as a medium to provide data of the programs of the present invention via a communication line, a carrier wave can also be used.

Detailed configurations and detailed actions of the devices and so forth of the radiation imaging system can also be appropriately modified without departing from the spirit of the present invention.

The invention claimed is:

1. A radiation imaging system comprising:
a radiation detector which detects received radiation and generates image data;
a console which is communicable with the radiation detector;
an imaging selection button to select one imaging from among imagings contained in an examination; and
a notifying unit which notifies whether the imaging correlated with the imaging selection button is still image shooting or moving image shooting by at least one of a color and a screen design.

2. The radiation imaging system according to claim 1, wherein
the console includes a display device, and
the display device displays the imaging selection button.

3. The radiation imaging system according to claim 1, wherein
the notifying unit displays information on each of the imagings on an examination screen, where information on each of imagings to be performed in an examination is displayed during the examination, by at least one of the color and the screen design for each of the imagings, each imaging being the still image shooting or the moving image shooting.

4. The radiation imaging system according to claim 1, wherein the notifying unit displays the imaging selection button by at least one of the color and the screen design for each of the imagings, each imaging being the still image shooting or the moving image shooting.

5. The radiation imaging system according to claim 1, wherein the screen design is an icon.

6. A console comprising:
a display device which displays an imaging selection button to select one imaging from among imagings contained in an examination; and
a notifying unit which notifies whether the imaging correlated with the imaging selection button is still image shooting or moving image shooting by at least one of a color and a screen design, wherein
the console is communicable with a radiation detector which detects received radiation and generates image data.

7. The console according to claim 6, wherein
the notifying unit displays information on each of the imagings on an examination screen, where information on each of imagings to be performed in an examination is displayed during the examination, by at least one of the color and the screen design for each of the imagings, each imaging being the still image shooting or the moving image shooting.

8. The console according to claim 6, wherein
the notifying unit displays the imaging selection button by at least one of the color and the screen design for each of the imagings, each imaging being the still image shooting or the moving image shooting.

9. The console according to claim 6, wherein the screen design is an icon.

10. A non-transitory computer readable storage medium storing a program causing a computer of a console which is communicable with a radiation detector which detects received radiation and generates image data to:
cause a display device to display an imaging selection button to select one imaging from among imagings contained in an examination; and
perform control to notify whether the imaging correlated with the imaging selection button is still image shooting or moving image shooting by at least one of a color and a screen design.

11. The non-transitory computer readable storage medium storing the program according to claim 10, wherein
the program causes the computer to perform the control to display information on each of the imagings on an examination screen, where information on each of imagings to be performed in an examination is displayed during the examination, by at least one of the color and the screen design for each of the imagings, each imaging being the still image shooting or the moving image shooting.

12. The non-transitory computer readable storage medium storing the program according to claim 10, wherein
the program causes the computer to perform the control to display the imaging selection button by at least one of the color and the screen design for each of the imagings, each imaging being the still image shooting or the moving image shooting.

13. The non-transitory computer readable storage medium storing the program according to claim 10, wherein the screen design is an icon.

* * * * *